US009248071B1

(12) United States Patent
Benda et al.

(10) Patent No.: US 9,248,071 B1
(45) Date of Patent: Feb. 2, 2016

(54) WALKING, REHABILITATION AND EXERCISE MACHINE

(71) Applicant: Ergoflex, Inc., Carpentersville, IL (US)

(72) Inventors: Scott Benda, West Dundee, IL (US); Randy Klemm, West Dundee, IL (US); Tim Klemm, West Dundee, IL (US)

(73) Assignee: Ergoflex, Inc., Carpentersville, IL (US)

( * ) Notice: Subject to any disclaimer, the term of this patent is extended or adjusted under 35 U.S.C. 154(b) by 511 days.

(21) Appl. No.: 13/834,659

(22) Filed: Mar. 15, 2013

(51) Int. Cl.
*A61M 11/00* (2006.01)
*A61H 1/00* (2006.01)

(52) U.S. Cl.
CPC ........................................ *A61H 1/00* (2013.01)

(58) Field of Classification Search
CPC ... A61H 1/00; A61H 1/02; A61H 2001/0211; A61H 1/0237; A61H 1/0244; A61H 1/0262; A61H 1/0266; A61H 2201/0119; A61H 2201/1207; A61H 2201/1215; A61H 2201/1253; A61H 2201/1261; A61H 2201/1269; A61H 2201/1276; A61H 2201/16; A61H 2201/164; A61H 2201/1642; A61H 2203/04; A61H 2203/0406; A61H 2205/10; A61H 2205/102; A61H 2205/106; A61H 2205/112; A63B 22/0664; A63B 22/0694; A63B 22/108; A63B 22/001; A63B 22/0015; A63B 2022/0025; A63B 2022/225
USPC .................. 482/51–54, 66–70; 601/5, 23, 24, 601/27–35, 84, 112
See application file for complete search history.

(56) References Cited

U.S. PATENT DOCUMENTS

| | | | | |
|---|---|---|---|---|
| 4,207,879 | A * | 6/1980 | Safadago et al. | 606/242 |
| 5,916,065 | A * | 6/1999 | McBride et al. | 482/57 |
| 7,163,492 | B1 * | 1/2007 | Sotiriades | 482/51 |
| 8,007,405 | B2 * | 8/2011 | Burnfield et al. | 482/7 |
| 8,795,139 | B2 * | 8/2014 | Zhang et al. | 482/52 |
| 2002/0055420 | A1 * | 5/2002 | Stearns et al. | 482/52 |
| 2005/0043145 | A1 * | 2/2005 | Anderson et al. | 482/52 |
| 2006/0009330 | A1 * | 1/2006 | Lo | 482/52 |
| 2009/0209395 | A1 | 8/2009 | Maresh et al. | |
| 2014/0274574 | A1 * | 9/2014 | Shorten et al. | 482/52 |
| 2015/0165265 | A1 * | 6/2015 | Tholkes et al. | |

FOREIGN PATENT DOCUMENTS

EP 1 566 203 A2 8/2005

* cited by examiner

*Primary Examiner* — Steven Douglas
(74) *Attorney, Agent, or Firm* — Mathew R. P. Perrone, Jr.; Joseph Whang

(57) ABSTRACT

A walking rehabilitation and exercise machine in the form of an elliptical style machine closely replicates the mechanical foot motions of walking, while incorporating hand motion to help a disabled or injured person retrain muscles in a proper walking gait and improve physical fitness. The device includes an electrically adjustable seat, independent left or right electrically adjustable stride and an electric flywheel drive to assist the operator.

12 Claims, 12 Drawing Sheets

WALKING, REHABILITATION AND EXERCISE MACHINE

This invention relates to a walking rehabilitation and exercise machine, and more particularly, to a walking rehabilitation and exercise machine, which can be adjusted to exercise legs of a person in a different fashion.

BACKGROUND OF THE INVENTION

Walking rehabilitation and exercise machines are commonly used for many purposes. In some cases, a walking rehabilitation and exercise machine is used for physical fitness. In other situations, a walking rehabilitation and exercise machine is used for physical rehabilitation for physical therapy purposes.

The very serious cases requiring physical therapy involve a person whose injury requires that person to relearn how to walk. In some cases, there is an exterior metal skeleton, known as an exoskeleton, which can be strapped to the person activated by an outside power source. These devices are expensive and complicated to use. These devices are typically too expensive for home use, or use by small therapy clinics. Thus, their availability is limited.

These exercise devices of the prior art also seem not intended to retrain a person for a proper walking gait. They also do not offer other desirable features. For example, they lack the support that person needs, while working to regain a good walking gait or carry out other functions. Furthermore, they prevent a slow warm-up, which a person needs for rehabilitation. Additionally, they cannot be adjusted relative to the skills for one side of the body or the other.

Adjustment between standing, partially standing, and sitting is also lacking in the machines of the prior art. Partially standing is a position necessary for a person to increase leg strength, which can lead to more efficient walking. To that end, those adjustments become critical. Yet they are absent from the standard exercise machine.

A standard fitness walking rehabilitation and exercise machine is not suitable for the serious aspects requiring extensive physical therapy. Such a device cannot be adjusted for a particular person. This is especially true when that person is adversely affected on one side of the body more than the other. To design a device and compensate for that defect is very difficult. Such devices generally have a requirement for substantially uniform motion from both sides of the body.

Yet, for certain injuries, such uniform motion is a physical impossibility. To that end, the advantages of having the walking rehabilitation and exercise machine be adjustable for the particular purpose can prove very useful. Not only can a person adjust the device according to their desires and needs, the appropriate parts of the body can receive the desired exercise.

Another desired feature for an exercise machine is the ability to move feet in a reverse motion in order to help loosen hamstrings. This movement is very important for a wheelchair-bound person to loosen those muscles and enable that person to fully benefit from this device. The prior art devices do not offer that option to a person substantially confined to wheelchair.

Thus, it may be seen that such adjustability applied to this device in a simple fashion offers great advantages for those people trying to recover from serious injuries.

SUMMARY OF THE INVENTION

Among the many objectives of this invention is the provision of an adjustable walking rehabilitation and exercise machine.

A further objective of this invention is the provision of a durable walking rehabilitation and exercise machine.

Yet a further objective of this invention is the provision of a walking rehabilitation and exercise machine to provide for treatment of a person with severe injuries.

A still further objective of this invention is the provision of a walking rehabilitation and exercise machine to replace an external skeleton.

Another objective of this invention is the provision of a walking rehabilitation and exercise machine to adjust a workout range for a person.

Yet another objective of this invention is the provision a walking rehabilitation and exercise machine, usable for a standing workout.

Still, another objective of this invention is the provision of a walking rehabilitation and exercise machine, usable for a sitting workout.

Also, an objective of this invention is the provision of a walking rehabilitation and exercise machine, usable for a partially sitting workout.

A further objective of this invention is the provision of a durable walking rehabilitation and exercise machine to loosen hamstrings of a person.

These and other objectives of the invention (which other objectives become clear by consideration of the specification, claims and drawings as a whole) are met by providing a walking rehabilitation and exercise machine, preferably in the form of an elliptical style machine, that closely replicates the mechanical foot motions of walking, while incorporating hand motion to help a disabled or injured person retrain muscles in a proper walking gait and improve physical fitness. The device includes an electrically adjustable seat, independent left or right electrically adjustable stride and an electric flywheel drive to assist the operator.

BRIEF DESCRIPTION OF THE DRAWINGS

Throughout the figures of the drawings, where the same part appears in more than one figure of the drawings, the same number is applied thereto.

DESCRIPTION OF THE PREFERRED EMBODIMENTS

Figure 1:
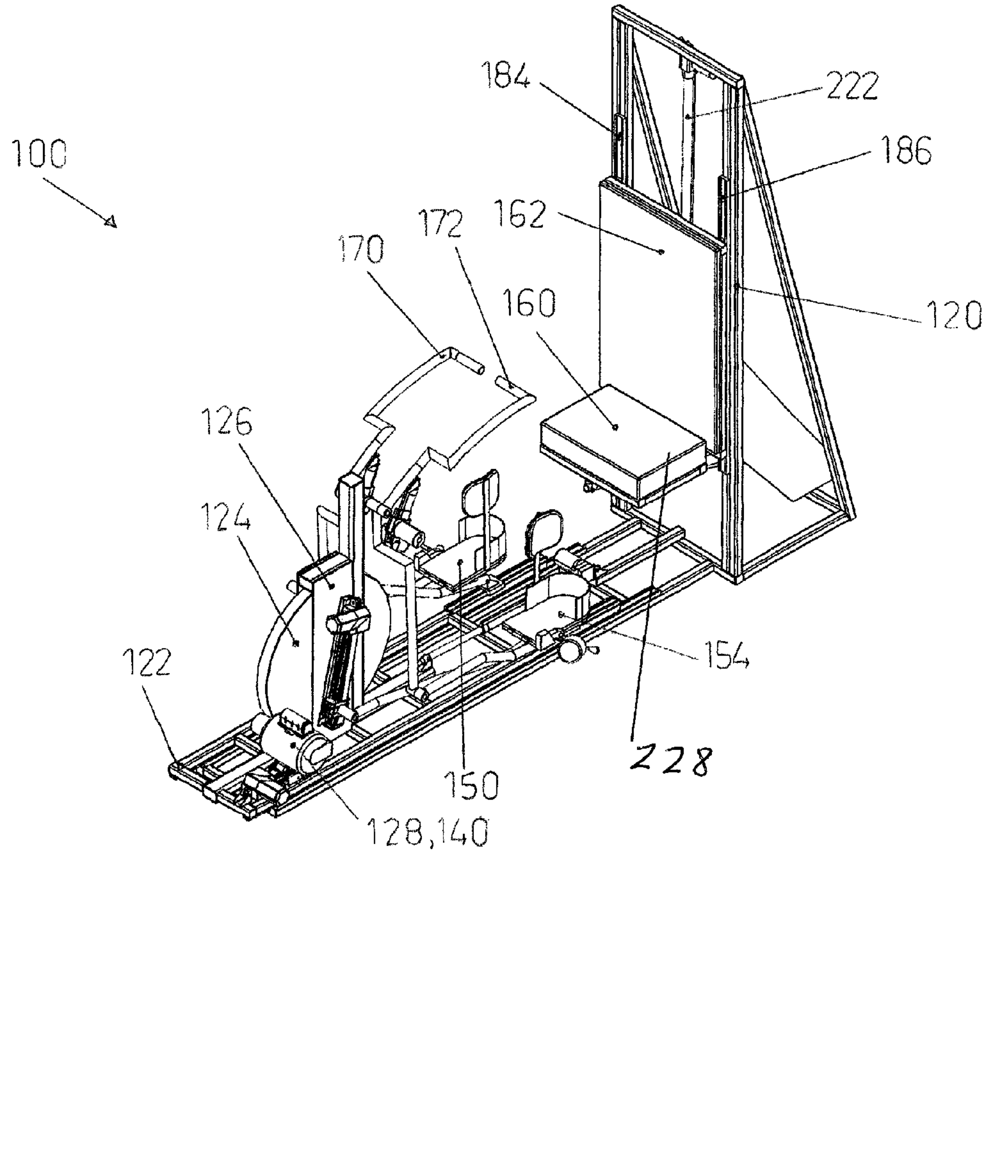
FIG. 1 depicts a perspective view of a walking rehabilitation and exercise machine 100 of this invention.

Reference will now be made in detail to several embodiments of the invention that are illustrated in accompanying drawings. Whenever possible, the same or similar reference numerals are used in the drawings and the description to refer to the same or like parts or steps. The drawings are in simplified form and are not to precise scale. For purposes of convenience and clarity only, directional terms such as top, bottom, left, right, up, down, over, above, below, beneath, rear, and front, may be used with respect to the drawings. These and similar directional terms are not to be construed to limit the scope of the invention in any manner. The words attach, connect, couple, and similar terms with their inflectional morphemes do not necessarily denote direct or intermediate connections, but may also include connections through mediate elements or devices.

For the walking rehabilitation and exercise machine of this invention, the foot motions of proper walking gait are emphasized, while at the same time providing hand motion and electric drive to help people with physical disabilities or injuries retrain their muscles in a walking motion, while the same time providing exercises to the muscles. This walking rehabilitation and exercise machine has an electrically adjustable stride length, the ability to perform exercise from the seated, semi-seated, or standing position. It also has a power source with a variable speed control and clutch release, which can completely disengage the drive motor. Support features include harness straps whether for feet or body, or pads to enable a person with limited physical abilities to safely use the device.

Another feature of this machine is the ability to adjust, so that it is possible to move feet in a reverse motion. This action helps to loosen hamstrings, which is very important for a wheelchair-bound person. To loosen muscles and enable that person to fully benefit from this device is very desirable.

Figure 2:
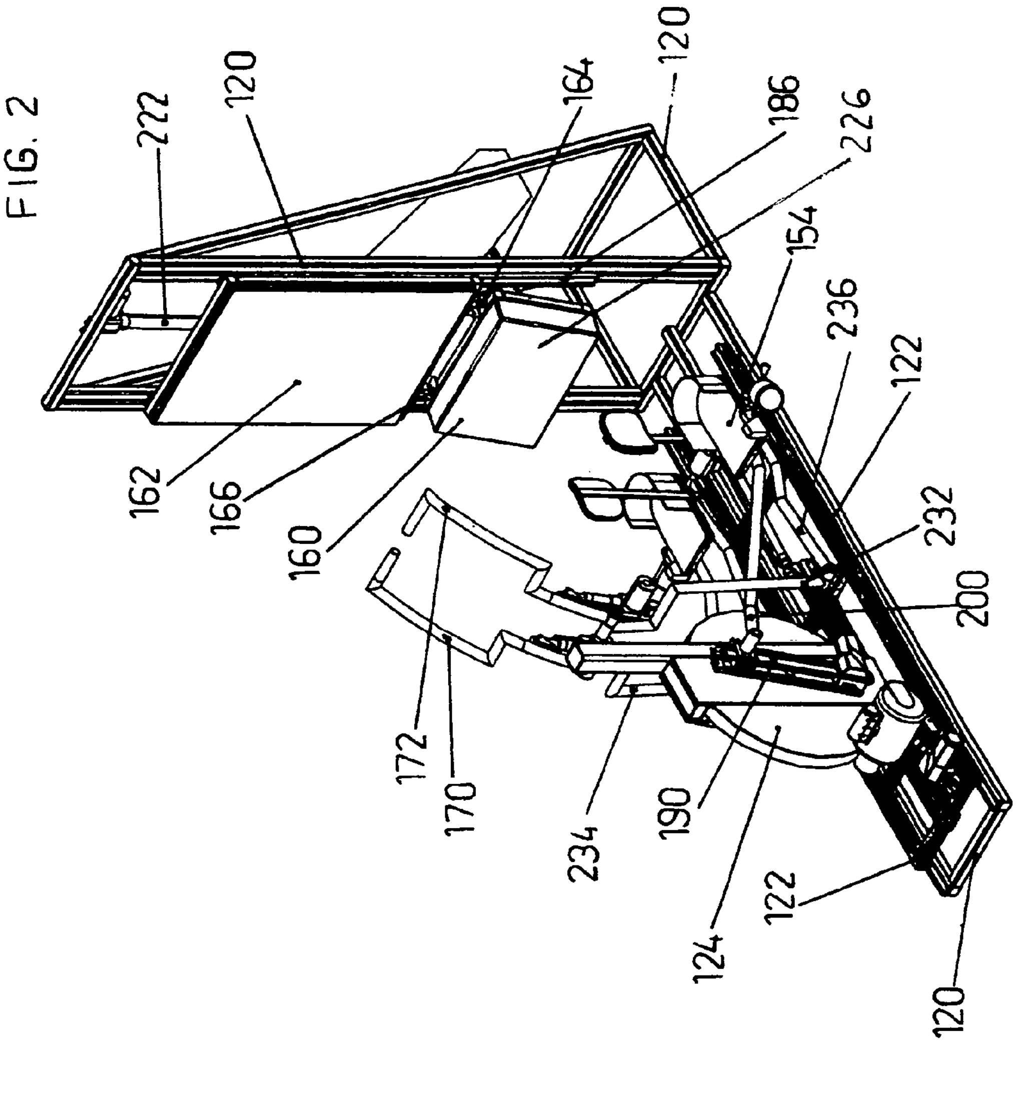
FIG. 2 depicts a perspective view of a walking rehabilitation and exercise machine 100 of this invention as in FIG. 1 except the seat back is raised and seat bottom tilted down.

Referring now to FIG. 1 and FIG. 2, a walking rehabilitation and exercise machine 100 has a machine frame 120 with an elliptical base assembly support 122. Flywheel 124 is supported on elliptical base assembly support 122 by flywheel console 126. Drive motor 128 has drive wheel 130 to operate flywheel 124. Flywheel 124 may also be operated manually by disengaging drive motor 128.

As the flywheel 124 turns, the left foot linkage 200 and the right foot linkage 202 (FIG. 5) that are connected to the flywheel shaft 268 move a right foot plate 150 with right foot base 152 and a left foot plate 154 with left foot base 156 in a preferably slightly elliptical motion. At the same time or a different time, right handle 170 or left handle 172 can be moved in a back-and-forth motion at the same time or separately.

The walking rehabilitation and exercise machine 100 has a frame 120 with of an elliptical base assembly support 122 to serve as a housing. Seat bottom 160 and seat back 162, with right seat track 184 and left seat track 186, lead to a seat down position 226 or a seat up position 228, as desired. The seat bottom 160 and seat back 162 may be connected by first seat hinge 164 and second seat hinge 166.

The seat back 162 may also be connected to the right seat track 184 and the left seat track 186. The seat bottom 160 and seat back 162, with the supporting elements, form the seat assembly. The seat bottom 160 and seat back 162, together with the other components, travel vertically with a seat raising actuator 222 and a seat tilting actuator 224, which are explained in more detail in following figures. The right seat track 184 and left seat track 186 are mounted to a machine frame 120.

In FIG. 2 right seat track 184 and left seat track 186 have the seat back 162 raised and seat bottom 160 tilted downwardly, so that walking rehabilitation and exercise machine 100 can accommodate a standing user. The lifting motion of the seat back 162 is accomplished by an electric seat raising actuator 222 shown in following figures. The tilting of the seat bottom 160 is accomplished by an electric seat tilting actuator 224 illustrated more clearly and identified in following figures.

The elliptical base assembly support 122 is shaded to show the overall base that the elliptical machine rests upon. The elliptical base assembly support 122 rests on the machine frame 120 identified more clearly in FIG. 3. Elliptical base assembly support 122 slides forward and back by means of an electric elliptical base actuator 230 to best accommodate the size and position of the operator whether that person is large or small, sitting or standing.

Left radial track actuator 190 is an electrically powered track actuator mounted on the flywheel shaft, parallel to the flywheel 124, and rotates with the flywheel 124. This actuator 190 connects to the left foot linkage 200, with a similar structure for the right foot linkage 202. The rotation of the flywheel 124 and track actuator 190 causes the left foot plate 154 to move back-and-forth in a slightly elliptical motion. The foot plates 150 and 154 are connected to a left foot linkage 200 and a right foot linkage 202, which are in turn connected to left horizontal linkage 236 and right horizontal linkage 238. Left horizontal linkage 236 and right horizontal linkage 238 are connected respectively to left vertical linkage 232 and right vertical linkage 234.

Figure 4:
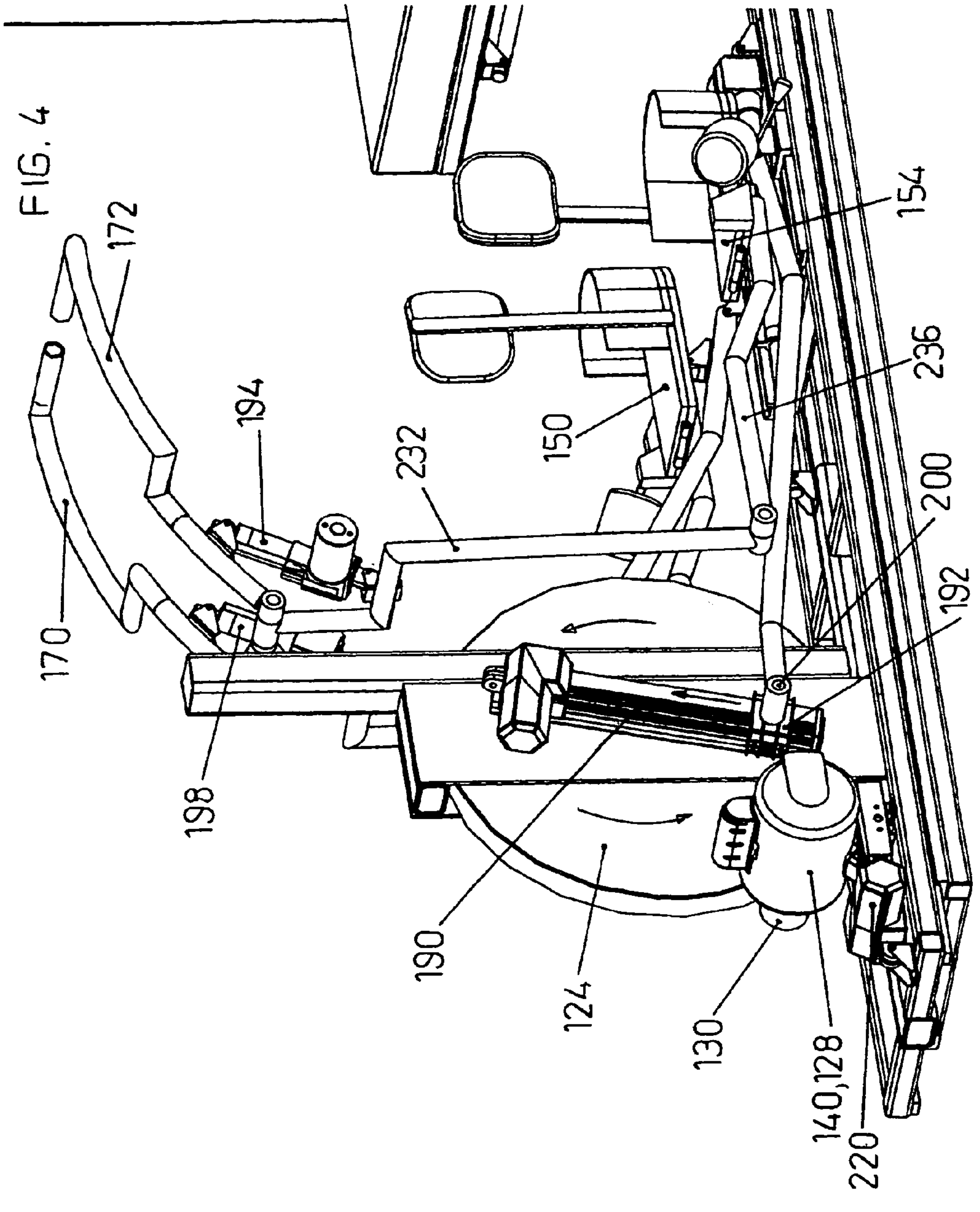
FIG. 4 depicts a walking rehabilitation and exercise machine 100 of this invention showing the flywheel 124.

Left vertical linkage 232 and right vertical linkage 234 cause right handle 170 and left handle 172 to move back and forth. Reference to right and left means that the right side has a mirror image of all these linkages and mechanisms and works in the same way. FIG. 4 explains the linkages and movements in more detail.

Figure 3:
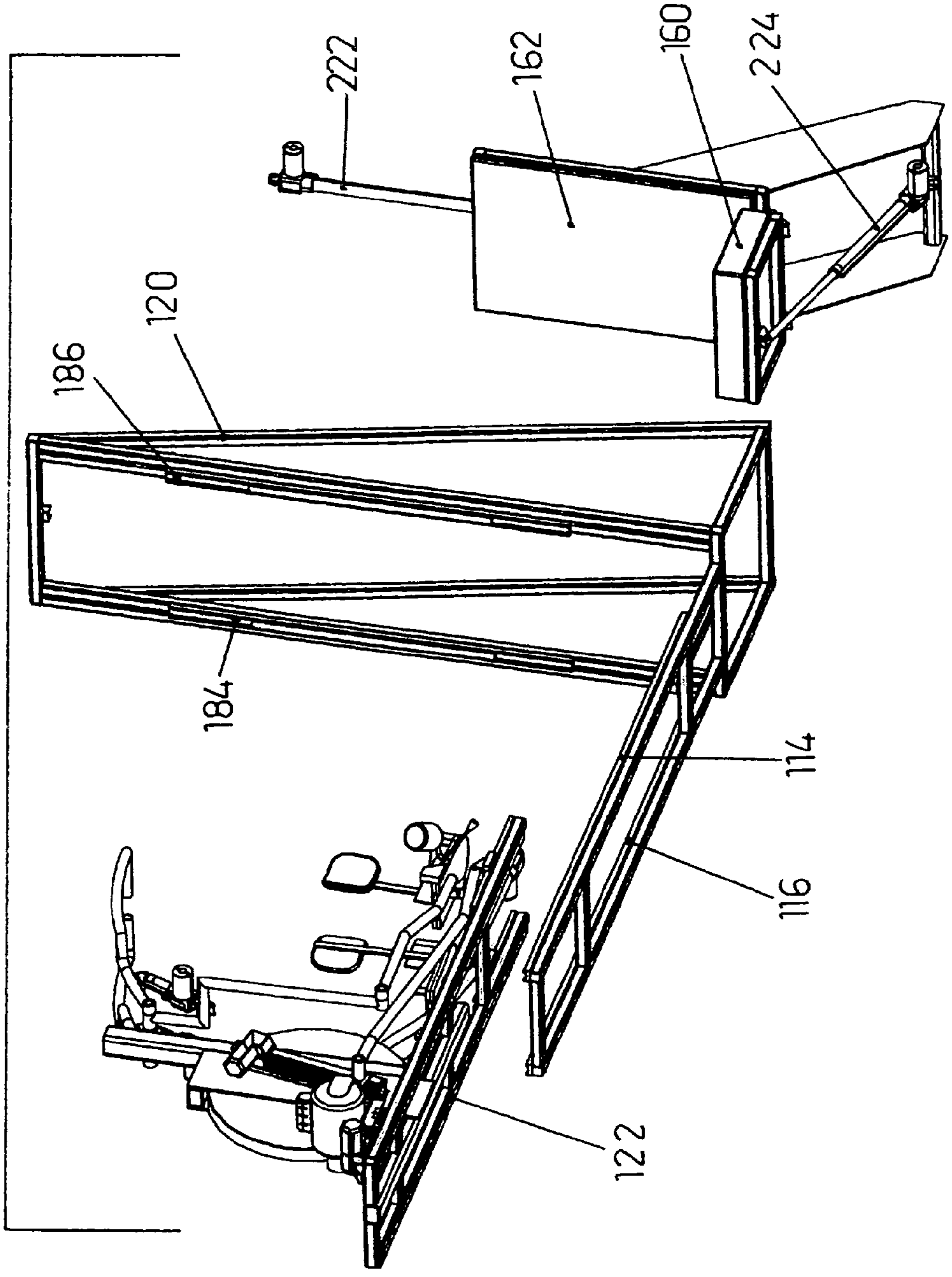
FIG. 3 depicts a partially exploded perspective view of a walking rehabilitation and exercise machine 100.

FIG. 3 identifies three major sub-assemblies. The first is identified as elliptical base assembly support 122 of the walking rehabilitation and exercise machine 100. The second is the machine frame 120. The third is the seat assembly formed from seat bottom 160, seat back 162, seat raising actuator 222, and seat tilting actuator 224. Elliptical base assembly support 122 attaches on top of the left horizontal track 114 and right horizontal track 116 of the machine frame 120. The elliptical base assembly support 122 slides forward and back on the machine frame 120 by means of an electrical elliptical base actuator 230.

The seat assembly attaches to the front of the vertical rails of the machine frame 120. The seat back 162 attaches to the machine frame 120 and is lifted or lowered by means of an electrical seat raising actuator 222, which connects to the seat assembly and machine frame 120. The seat bottom 160 is tilted from or to a horizontal or seat up position 226 to a near vertical position or seat down position 228 by means of an electrical drive actuator 224 including seat raising actuator 222 and seat tilting actuator 224.

Figure 5:
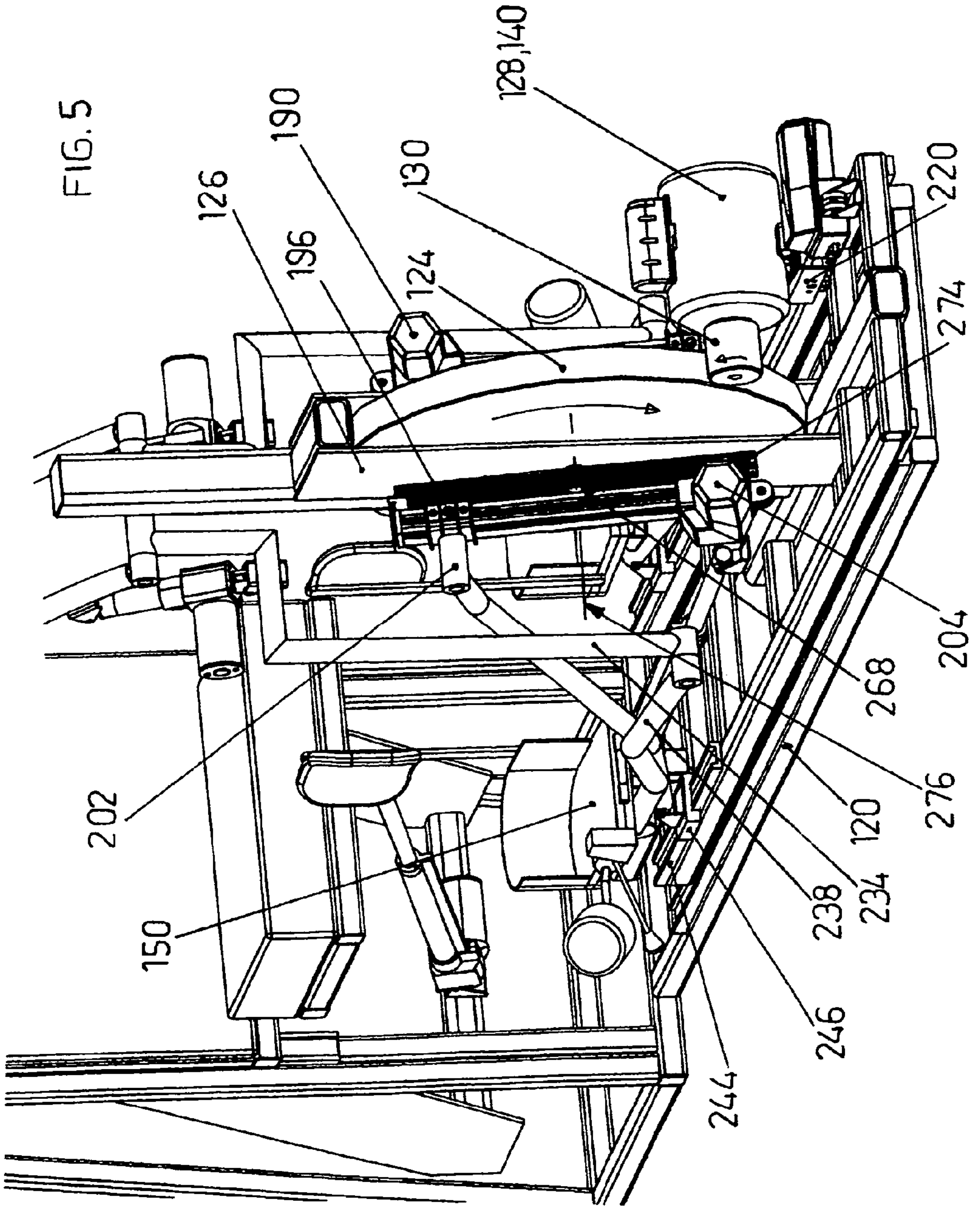
FIG. 5 depicts a walking rehabilitation and exercise machine 100 of this invention showing the left radial track actuator 190 and right radial track actuator 204.

FIG. 4 shows a close-up view of the walking rehabilitation and exercise machine 100 mechanisms, as well as the electric drive motor 128. Drive motor 128 operates drive wheel 130, which drives the flywheel 124 at the flywheel console 126 and the flywheel shaft 268, when the drive wheel 130 is in contact with the flywheel 124. The motor 128 is mounted on a horizontal electrical track actuator 220 that can move the motor 128 with the drive wheel 130 toward and away from the flywheel 124. This action causes contact and drive of the flywheel 124. By disengaging the drive wheel 130, the flywheel 124 can be rotated by manpower from the operator. This is also shown in FIG. 5.

The electric drive motor 128 may have a clutch 140 to limit the transmitted power to the flywheel 124 for safety. Also attached to the flywheel 124 is the left radial track actuator 190, which is mounted to the flywheel shaft 268 and rotates with the flywheel 124, which is more clearly shown in FIG. 5.

Left radial actuator saddle 192 connects to the left foot linkage 200. The saddle 192 can be moved radially toward the middle of the track actuator 190 with the electric power of the actuator 190. When the saddle 192 moves radially, it adjusts the foot stride since the circular path connected to the front of the left foot linkage 200 determines the stride of the left foot plate 154 and the left foot base 156. Right foot plate 150 and right foot base 152 operate in a similar fashion.

The horizontal back and forth movement or stride of the left foot plate 154 and the left foot base 156, and right foot plate 150 and right foot base 152 is equal to the diameter of the circular movement of the left radial actuator 190 and right radial actuator 204. Cooperation between the left radial actuator 190 the right radial actuator 204 forms further cooperation between the left radial actuator saddle 192, the left handle actuator 194, the right radial actuator saddle 196 and the right handle actuator 198.

When the saddles 192 or 196 travel all the way to the flywheel axis 276, the foot stride and hence the movement of the right foot plate 150 or the left foot plate 154 becomes zero. The actuators 190 or 204 are positioned so that the saddles 192 and 196 can travel from an outer radius of approximately nine inches and travel all the way to the flywheel axis 276 but no further. Hence the stride can be adjusted to 18 inches maximum (nine inches radius or 18 inches diameter) and it can be stopped anywhere in between zero and 18 inches.

The same can be done with the left side radial track actuator 190 and foot linkages 200 or right radial track actuator 204 and linkage 202 shown in following figures. This feature gives an operator the ability to work the left and right sides differently depending upon their abilities and needs. The left handle actuator 194 and right handle actuator 198 serve as linear electrical actuators to adjust the left handle 172 and right handle 170 positions to best suit the position and size of the operator.

These handle actuators 194 and 198 pivot back and forth with the movement of the left vertical linkage 232 and the right vertical linkage 234 and left horizontal linkage 236 and right horizontal linkage 238 for horizontal foot linkages 200 or 202. Hence, if the saddles 192 or 196 are positioned on the left radial track actuator 190 at the flywheel 124 axis, the left handle 172 movement also becomes zero. Likewise, left handle 172 motion increases as the saddle 192 moves away from the flywheel 124 axis. The same applies to the right side movements.

FIG. 5 shows a slightly different forward view of the flywheel 124 and components. Arrow 276 points to the horizontal flywheel axis about which the flywheel 124 rotates. The flywheel axle 268 which is fixed to the right axle bracket 274 and goes through the flywheel console 126 to the left axle bracket that cannot be seen in this view, but is a mirror image of that shown on the right side.

The electrical track actuator 204 is attached to the axle bracket 274 which is shaded in this view for clarity. As the flywheel 124, right axle bracket 274, and right electrical track actuator 204 spin, the forward end of the right foot linkage 202 moves in a circle. The circle diameter is directly determined by the position of the right radial actuator saddle 196 on the actuator track 204 and the distance from the flywheel axis 276. As the saddle 196 spins in a circle with the flywheel 124 the right foot linkage 202 moves with it and causes the right foot plate 150 to move forward and back.

The right footplate 150 is connected to the right foot carriage 246 which slides on the right foot rail 244. Right foot rail 244 and right foot carriage 246 are a rail and carriage combination for smooth linear motion. Right foot carriage 246 is secured to the right foot rail 244 so it can only travel linearly, so that the right foot plate 150 cannot be inadvertently pulled off by an operator if he or she has a muscle spasm.

FIG. 5 also shows another view of the electric drive motor 128, drive wheel 130 and drive actuator 220. The drive actuator 220 moves the electric drive motor 128 and drive wheel 130 forward and back to engage or disengage the drive from the flywheel 124 enabling the walking rehabilitation and exercise machine 100 to be used in a fully manual or fully electrically driven mode.

Figure 6:
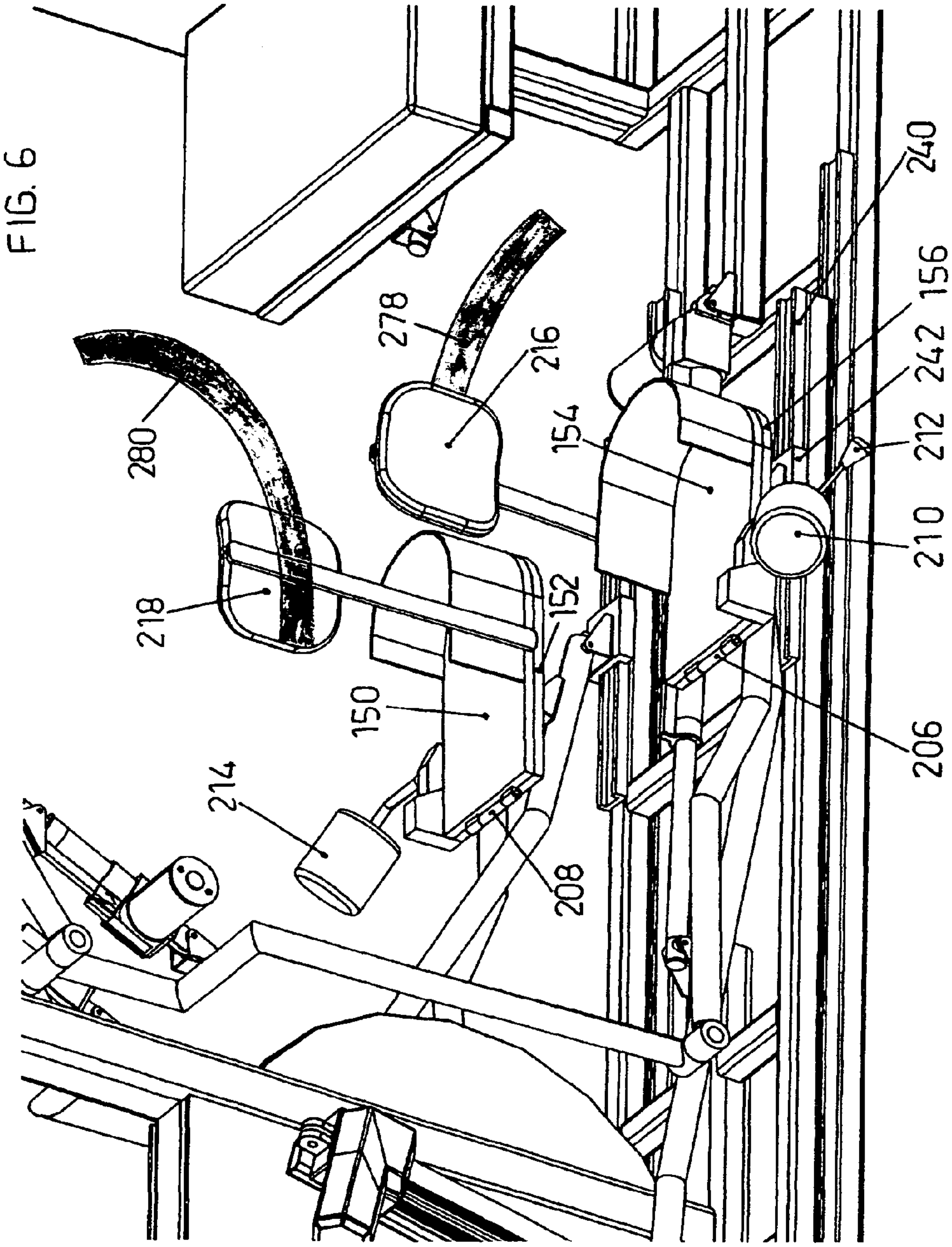
FIG. 6 depicts a walking rehabilitation and exercise machine 100 of this invention showing the function of right foot plate 150 and left foot plate 154.

FIG. 6 shows a close-up of the right foot plate 150 with right foot base 152 and left foot plate 154 with left foot base 156, which are similar mirror images. Left foot hinge 206 permits left foot plate 154 to move. Right foot hinge 208 permits right plate 150 to move. Left foot pad 210 swings on top of a left foot to be temporarily secured by left foot pad lever 212. Right foot pad 214 receives a right foot to be temporarily secured by right foot pad lever 212. Left leg support 216 extends from left foot plate 154. Right leg support 218 extends from right foot plate 150.

More particularly, left strap 278 and right leg strap 280 support the appropriate leg on left and right foot plates 154 and 150. The left foot of the user rests on the left foot plate 154 and the left foot pad 210 swings over the foot and locks in place with the left foot pad lever 212. The left leg strap 278 wraps around the user's left leg at the calf and has a securing device. A standard hook and loop assembly is a suitable securing device for holding the strap 278 and is available under the registered trademark VELCRO, owned by Velcro Industries B.V. LIMITED LIABILITY COMPANY NETHERLANDS Castorweg 22-24 Curacao NETHERLANDS ANTILLES.

A left foot hinge 206 and a right foot hinge 208 connect the left foot plate 154 and right foot plate 150 to their corresponding left foot base 156 and right foot base 152. When the operator uses this walking rehabilitation and exercise machine 100, the left foot moves in a natural walking gait where the person's heel raises as the foot moves forward and pivots down when the foot moved back. This pivoting action is accommodated by means of the left foot hinge 206 between the left foot plate 154 and left foot base 154. The same is true of the right foot and leg of a user of the walking rehabilitation and exercise machine 100.

Figure 7:
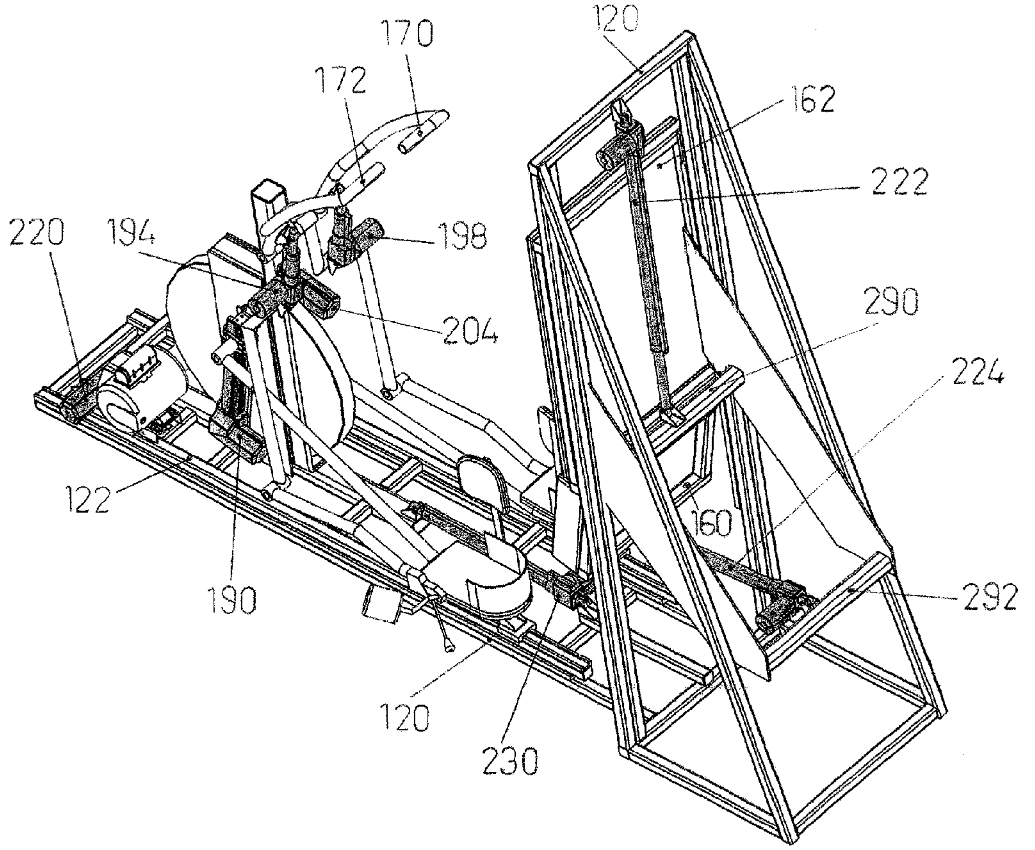
FIG. 7 depicts a walking rehabilitation and exercise machine 100 of this invention focusing on the eight different electrical actuators which are shaded for clarity.

FIG. 7 identifies and describes the eight electrical actuators used on this machine. These actuators are typical commercially available and consist of two styles; linear actuators and track actuators. Five of the actuators are linear electric actuators and are identified as left handle actuator 194, right handle actuator 198, seat raising actuator 222, seat tilting actuator 224 and elliptical base actuator 230. All of these commercially available linear electric actuators have an electric motor that extends and retracts a shaft, thereby moving two connected pieces at each end.

Left handle actuator 194 and right handle actuator 198 extend and retract to reposition the right handle 170 and left handle 172 to best suit the size and location of the user. The user may be seated or standing or somewhere in between.

Seat raising actuator 222 is connected to the machine frame 120 at the top thereof and the seat lifting bar seat lifting bar 290. As this seat raising actuator 222 extends and retracts it causes the seat back 162 to lower and rise. Seat tilting actuator 224 is connected to the seat bottom 160 and the seat tilting bar 292. As seat tilting actuator 224 extends, the seat tilts up to a horizontal position or seat down position 226. As this actuator retracts, the seat bottom 160 tilts down into seat down position 226.

The elliptical base actuator 230 is connected to the machine frame 120 and the elliptical base assembly support 122. As this actuator 230 extends, it slides the elliptical base 122 forward. As this actuator 230 retracts, it slides the elliptical base 122 back. This enables the person to be best positioned to use the walking rehabilitation and exercise machine 100 in a seated or standing position or anywhere in-between. These actuators 230 and the like are standard commercially available products that consist of an electric motor moving a shaft in an extending and contracting fashion to move two connected parts.

The track actuators are used in two applications on this walking rehabilitation and exercise machine 100. One is the electric drive actuator 220 that slides the electric motor and drive wheel forward and back, engaging and disengaging contact with the flywheel 124. The left radial actuator 190 and right radial actuator 204 are electric track actuators connected to the flywheel 124 that adjust the foot stride of the walking rehabilitation and exercise machine 100. All of the electric actuators can be started and stopped anywhere within their stroke and are controlled by means of push button controls.

Figure 8:
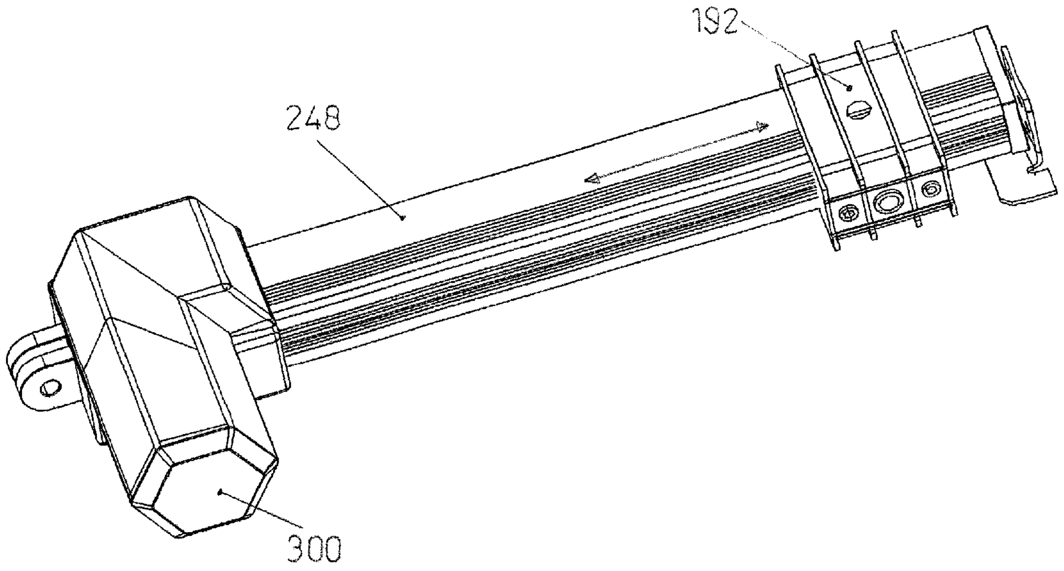
FIG. 8 depicts a typical commercially available electric track actuator such as left radial track actuator 190 for a walking rehabilitation and exercise machine 100 of this invention.

FIG. 8 shows a typical commercially available track actuator such as drive actuator 220 for the walking rehabilitation and exercise machine 100. This style of actuator 220 is used in three locations as described in FIG. 7. Actuator track 248 is connected to the left radial actuator saddle 192 and electric motor actuator 300. The electric motor 300 moves the saddle 192 along the track 248 in a back-and-forth motion. The left radial actuator 190 and the right radial actuator 204 are connected on opposing sides of flywheel 124.

Figure 9:
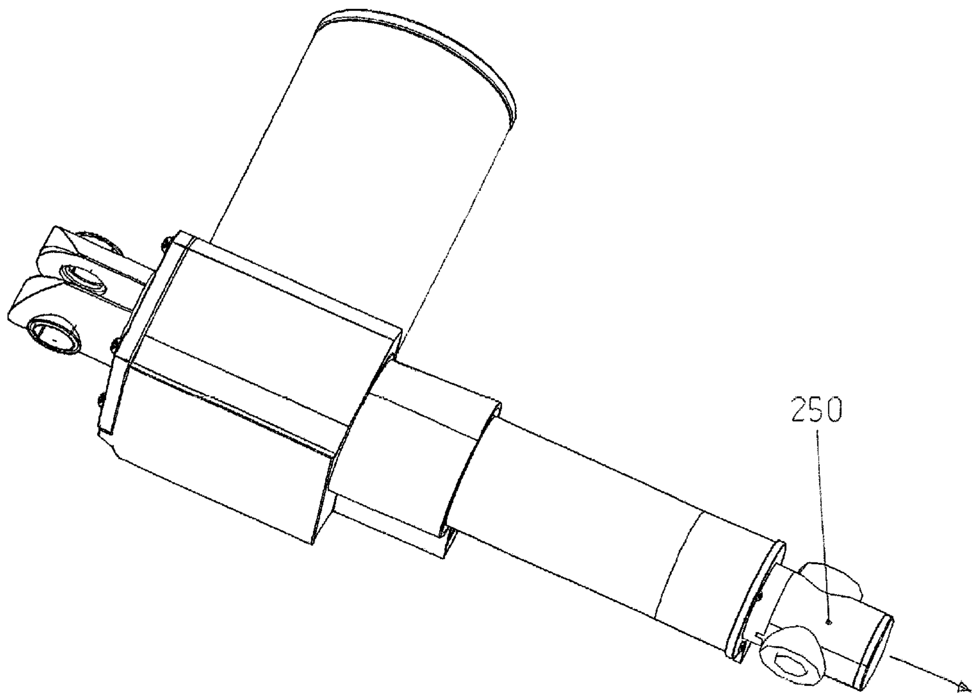
FIG. 9 depicts a typical commercially available electric linear actuator 222 for a walking rehabilitation and exercise machine 100 of this invention.

FIG. 9 shows a typical commercially available electric linear actuator as elliptical base actuator 230 for the walking rehabilitation and exercise machine 100. This style of electric actuator is used in 5 locations on the walking rehabilitation and exercise machine 100 as described in FIG. 7. The linear actuator 230 extends and retracts, sliding the shaft or actuator rod 250 back and forth, extending and contracting the actuator 230. It is controlled with push buttons in a standard control represented as shown in FIG. 10.

Figure 10:
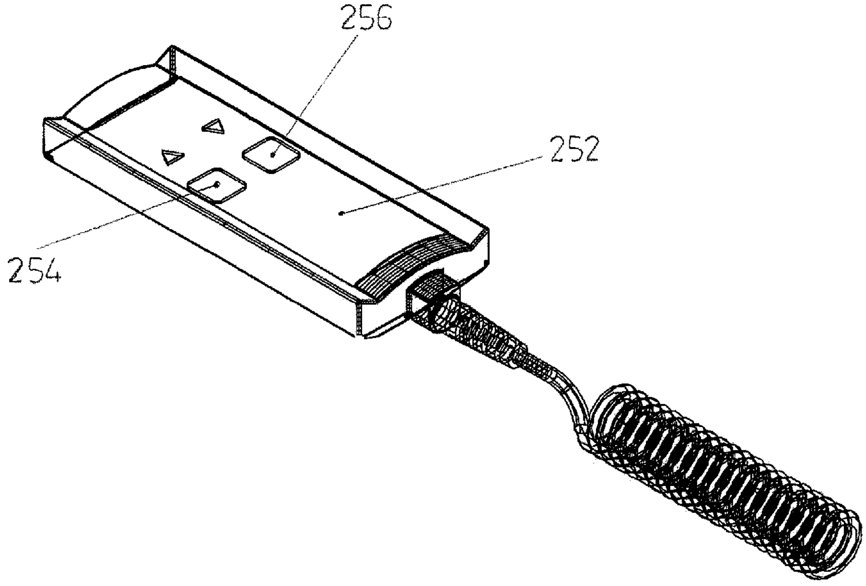
FIG. 10 depicts a commercially available pendant control 252 for electrical actuators for a walking rehabilitation and exercise machine 100 of this invention.

FIG. 10 shows a typical commercially available actuator control or pendant control 252 for the walking rehabilitation and exercise machine 100. This style controls one actuator using one pushbutton or extend button 254 to activate the actuator motion in one direction and the other button or retract button 256 to control actuation in the opposite direction. Hence one similar control can be used for each actuator but more desirably, several controls will be combined into one or two consoles. Standard commercially available control housings are available to control four or more actuators in one module, that is to say one control will have one pair of buttons for each actuator. Hence four actuators in one control would have eight buttons.

Figure 11:
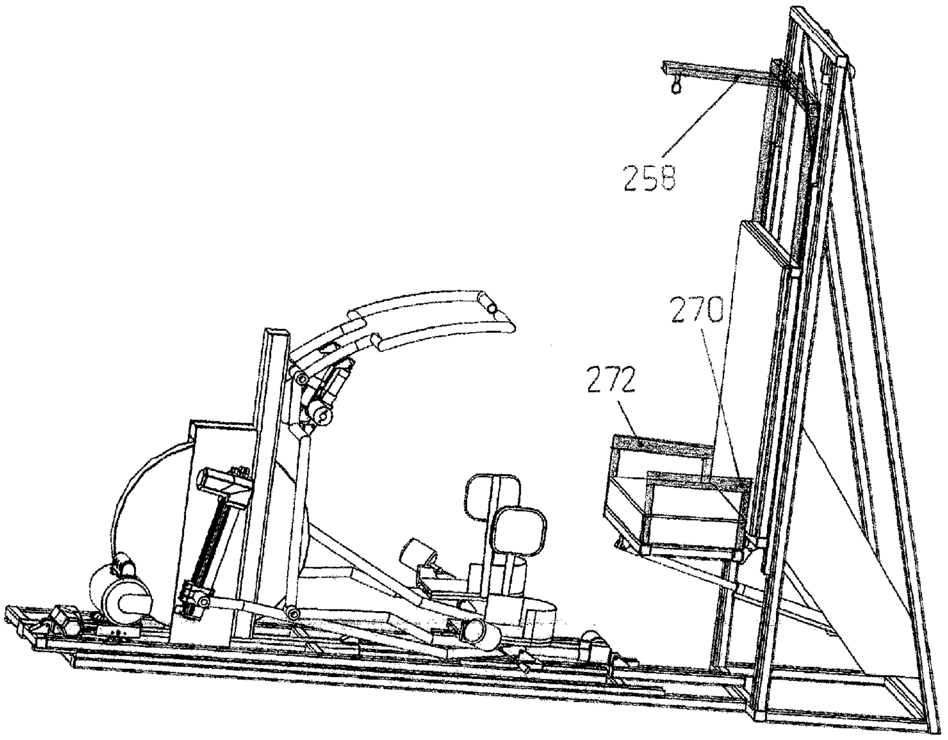
FIG. 11 depicts a detachable left hand rail 270 and right hand rail 272 to aid a handicapped user for a walking rehabilitation and exercise machine 100 of this invention.

FIG. 11 shows optional left hand rail 270 and right hand rail 272 for the walking rehabilitation and exercise machine 100. These rails 270 and 272 can be quickly attached and detached for ease of entering and leaving the seat bottom 160. This is important for a person transferring from a wheelchair. Not all users will need these rails 270 and 272, and it will depend upon their level of ability. However these rails 270 and 272 will provide assistance and support for a handicapped individual to stay in the proper position when using the device from a seated or standing position. Also, an overhead support bracket 258 can be used with numerous commercially available harnesses to assist handicapped persons and provide additional safety.

Figure 12:
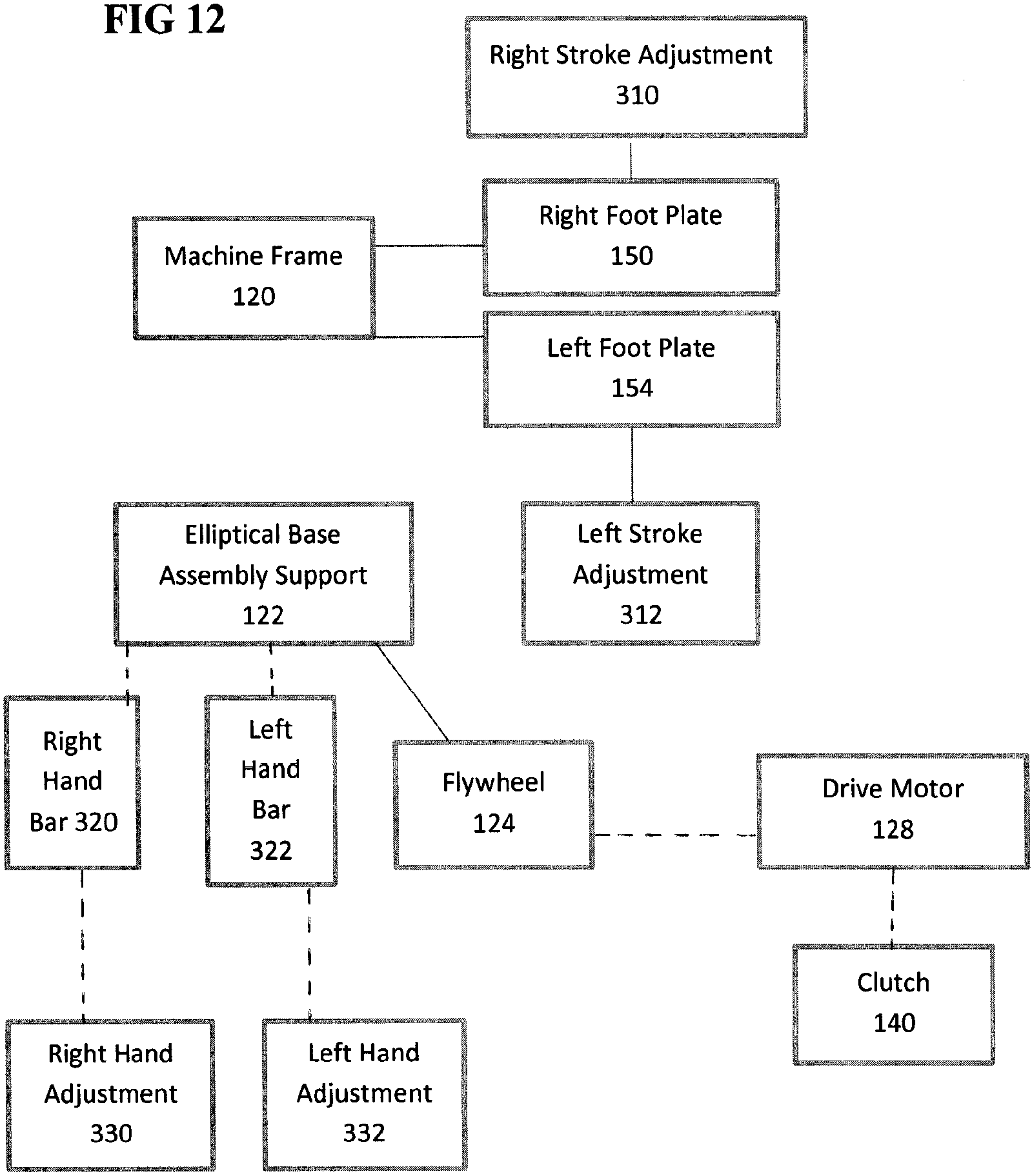
FIG. 12 is a walking rehabilitation and exercise machine 100 of this invention.

Turning now to FIG. 12, the walking rehabilitation and exercise machine 100 has machine frame 120 connected to elliptical base assembly support 122. The right foot plate 150 and the left foot plate 154 are connected to the machine frame 120. Right foot plate 150 has a right stroke adjustment unit 310 connected thereto. Left foot plate 154 has a as a left stroke adjustment 312 connected thereto. Both adjustment 312 and 310 are displayed in more specific embodiments in the above figures. On the elliptical base assembly support 122 is the flywheel 124. The drive motor 128 can operate the flywheel 124 if desired. Clutch 140 can separate drive motor 128 from the flywheel 124 if desired.

Right-hand adjustment 330 can optionally be connected to right-hand bar 320 for stroke adjustment if desired. Likewise, left hand adjustment 332 can optionally be connected to left-hand bar 322 for stroke adjustment if desired.

Thus, walking rehabilitation and exercise machine 100 provides a wide variety of exercises and positions for a person. This person can obtain exercise whether recovering from an injury were trying to maintain fitness. For recovery from an injury, the walking rehabilitation and exercise machine 100 can be adjusted provide a workout different for each side of the body. For fitness, such a differentiation is not needed. The walking rehabilitation and exercise machine 100 works well in either case.

This application—taken as a whole with the abstract, specification, claims, and drawings being combined—provides sufficient information for a person having ordinary skill in the art to practice the invention as disclosed and claimed herein. Any measures necessary to practice this invention are well within the skill of a person having ordinary skill in this art after that person has made a careful study of this disclosure.

Because of this disclosure and solely because of this disclosure, modification of this method and device can become clear to a person having ordinary skill in this particular art. Such modifications are clearly covered by this disclosure.

What is claimed and sought to be protected by Letters Patent of the United States is:

1. A walking, rehabilitation and exercise machine for replicating mechanical foot motions of walking, while incorporating hand motion to help a disabled or injured person retrain muscles in a proper walking gait and improve physical fitness, comprising:

the walking, rehabilitation and exercise machine having a machine frame the machine frame being connected to a base assembly support;

the walking, rehabilitation and exercise machine having an adjustable stride length for a left side and a right side of a body of a person to retrain muscles;

the base assembly support being an elliptical base assembly support;
a flywheel being supported on the elliptical base assembly support by a flywheel console;
the flywheel being mounted on a flywheel shaft;
a drive motor having a drive wheel to operate the flywheel;
the flywheel also being operable manually;
the drive motor being disengageable;
a left foot linkage and a right foot linkage being connected to the flywheel shaft;
the left foot linkage and the right foot linkage contributing to foot motions for a proper walking gait;
the left foot linkage moving a left foot and left base as the flywheel turns;
the right foot linkage moving a right foot plate and right base as the flywheel turns;
the left foot linkage having a left adjustable movement;
the right foot linkage movement having a right adjustable movement;
the left adjustable movement and the right adjustable movement being the same or different;
the flywheel being supported on the flywheel shaft
the left foot linkage and the right foot linkage having a connection to the flywheel shaft;
the connection being adjustable;
the left foot base and the right foot base moving in an elliptical motion;
a movable right handle on the frame cooperating with the right foot base;
a movable left handle on the frame cooperating with the left foot base;
the frame having a seat bottom and a seat back mounted thereon;
a right seat track and a left seat track being mounted on the frame;
the right seat track and the left seat track leading to a seat down position or a seat up position; and
the seat bottom and the seat back being connected by a first seat hinge and second seat hinge.

2. The machine of claim 1 further comprising:
the seat bottom and the seat back being mounted to the right seat track and the left seat track;
seat raising actuator or a seat tilting actuator adjusting a seat position the seat bottom and the seat back;
the seat bottom or the seat back being tilted downwardly to accommodate a standing user;
a lifting motion of the seat back being accomplished by the seat raising actuator; and
a tilting of the seat bottom being accomplished by the seat raising actuator.

3. The machine of claim 2 further comprising:
a) the elliptical base assembly support resting on the machine frame; and
b) an electric elliptical base actuator moving the elliptical base assembly support.

4. The machine of claim 3 further comprising:
a) a left radial track actuator being mounted on a first side of the flywheel shaft;
b) aright radial track actuator being mounted on a second side of the flywheel shaft;
c) the left radial track actuator and the right radial track actuator being electrically operable;
d) the left radial track actuator connecting to the left foot linkage;
e) the left radial track actuator connecting to the right foot linkage; and
f) the left radial track actuator and the right radial track actuator rotating with the flywheel.

5. The machine of claim 4 further comprising:
a) the left radial track actuator and the right radial track actuator causing the right foot plate and the left foot plate to move back-and-forth in a slightly elliptical motion;
b) the right foot plate and the left foot plate being connected to a left foot linkage and a right foot linkage respectively;
c) a left horizontal linkage and a right horizontal linkage being connected between the left foot linkage and the right foot linkage, and a left horizontal linkage and a right horizontal linkage;
d) the left horizontal linkage and the right horizontal linkage being connected respectively to a left vertical linkage and a right vertical linkage; and
e) the left vertical linkage and the right vertical linkage causing the right handle and the left handle to move back and forth.

6. The machine of claim 5 further comprising:
the elliptical base assembly support sliding forward and back on the machine frame by means of an electrical elliptical base actuator;
the seat assembly including a seat back and a seat bottom;
the seat bottom being tiltable from or to a horizontal or seat down position;
the left radial track actuator and the right radial track actuator permitting an adjustment of the walking, rehabilitation and exercise machine;
an electric drive motor operating the flywheel;
the electric drive motor having a motor shaft;
the electric drive motor having a drive wheel mounted on a motor shaft;
the drive wheel being adapted to engage the flywheel;
the drive wheel being adapted to turn the flywheel;
the drive wheel being movable from or to the flywheel as desired.

7. The machine of claim 6 further comprising:
the electric drive motor further including a clutch to limit power transmitted to the flywheel for safety;
a left radial actuator saddle connecting to the left foot linkage;
a right radial actuator saddle connecting to the right foot linkage;
the left radial actuator saddle and the right radial actuator adjusting a foot stride of the walking, rehabilitation and exercise machine;
the walking, rehabilitation and exercise machine being usable in a fully manual or fully electrically driven mode;
the right foot plate having a right foot base thereon;
the left foot plate having a left foot base thereon;
the right foot base receiving a right foot pad thereon;
the left foot base receiving a left foot pad thereon;
the left foot pad receiving a left foot; and
the right foot pad receiving a right foot.

8. The machine of claim 7 further comprising:
a) the left foot pad and the right foot pad each including a strap to hold a foot;
b) a left foot hinge connecting the left foot plate to a left foot base;
c) a right foot hinge connecting the right foot plate to a right foot base;
d) the machine including eight electrical actuators used on this machine;
e) the eight electrical actuators including five linear electric actuators and three track actuators;

f) the five linear electric actuators each having an electric motor that extends and retracts a shaft, thereby moving two connected pieces at each end; and g) the three track actuators providing movement back and forth along a track.

9. The machine of claim 8 further comprising:

a) the three track actuators being a motor actuator, a left handle actuator and a right handle actuator and a seat raising actuator;

b) the seat raising actuator permitting sitting or standing on the machine as desired;

c) the left handle actuator and right handle actuator each providing a handle adjustment; and h) the motor actuator moving the motor as desired.

10. The machine of claim 9 further comprising;

a) the eight actuators each including a pendant control;

b) a left hand rail and a right hand rail providing hand exercise.

11. A walking, rehabilitation and exercise machine comprising:

a machine frame being connected to a base assembly support;

a right foot plate and a left foot plate being connected to the machine frame;

the right foot plate having a right stroke adjustment unit connected thereto;

the left foot plate having left stroke adjustment unit connected thereto;

the base assembly support including a flywheel;

the base assembly support being an elliptical base assembly support;

an electric drive motor operating the flywheel;

a clutch for selectively separating the drive motor from the flywheel;

a right-hand adjustment on the machine being connected to a right-hand bar for stroke adjustment;

a left hand adjustment on the machine being connected to a left-hand bar for stroke adjustment;

a left foot linkage and a right foot linkage contributing to foot motions for a proper walking gait on the machine;

the left foot linkage moving a left footplate and left base as the flywheel turns;

the right foot linkage moving a right foot plate and right base as the flywheel turns;

the left foot linkage having a left adjustable movement;

the right foot linkage having a right adjustable movement;

the left adjustable movement and the right adjustable movement being the same or different;

the flywheel being supported on a flywheel shaft, the left foot linkage and the right foot linkage having a connection to the flywheel shaft;

the connection being adjustable;

the left foot base and the right foot base moving in an elliptical motion;

a movable right handle on the frame cooperating with the right foot base; and a movable left handle on the frame cooperating with the left foot base.

12. The machine of claim 11 further comprising:

a) the frame having a seat bottom and a seat back mounted thereon;

b) a right seat track and a left seat track being mounted on the frame;

c) the right seat track and the left seat track leading to a seat down position or a seat up position; and d) the seat bottom and the seat back being connected by a first seat hinge and second seat hinge.

* * * * *